United States Patent [19]

Collery et al.

[11] Patent Number: 5,525,598
[45] Date of Patent: Jun. 11, 1996

[54] GALLIUM (III) COMPLEXES IN PHARMACEUTICAL COMPOSITIONS

[75] Inventors: Philippe Collery, Reims, France; Bernhard Keppler, Richar Wagner Strasse 9A, 68723 Schwetzingen Frg, Germany

[73] Assignees: Phillippe Collery, Reims, France; Bernhard Keppler, Schwetzingen Frg, Germany

[21] Appl. No.: 178,241

[22] PCT Filed: Jul. 23, 1992

[86] PCT No.: PCT/EP92/01687

§ 371 Date: Jan. 24, 1994

§ 102(e) Date: Jan. 24, 1994

[87] PCT Pub. No.: WO93/02087

PCT Pub. Date: Feb. 4, 1993

[30] Foreign Application Priority Data

Jul. 25, 1991 [EP] European Pat. Off. ............ 91402093

[51] Int. Cl.⁶ .................................................. A61K 31/555
[52] U.S. Cl. ............................................................ 514/187
[58] Field of Search ............................................... 514/187

[56] References Cited

U.S. PATENT DOCUMENTS 4,529,593  7/1985  Warrell et al. ........................ 424/127

*Primary Examiner*—Kimberly Jordan
*Attorney, Agent, or Firm*—Dennison, Meserole, Pollack & Scheiner

[57] ABSTRACT

A method for treatment of viral infections or tumors, comprising administering a gallium complex of the formula:

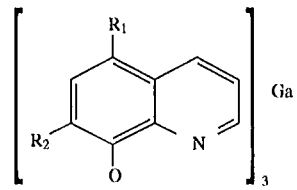

wherein $R_1$ represents hydrogen, a halogen or a sulfono group $SO_3M$ in which M is a metal ion such as potassium or sodium, and $R_2$ represents hydrogen, or $R_1$ is chlorine and $R_2$ is iodo.

4 Claims, No Drawings

GALLIUM (III) COMPLEXES IN PHARMACEUTICAL COMPOSITIONS

This application is a 371 of PCT/EP92/01687, filed Jul. 23, 1992.

The present invention relates to gallium (III) complexes, to the processes useful for their obtention and to their use as antitumoral and antiviral agents.

In medicine, gallium (III) compounds play a role in the following fields of research:

Firstly, Ga-67, a low energy-gamma-emitting radionuclide, is a very useful tumor diagnostic agent and has been used extensively (mostly as gallium-67 citrate) in the detection of a great number of human malignancies, ["Metal-based Antitumour Drugs" edited by M. F. Gielen, Freund Publishing House Ltd., 1988, Chapter 1; Ward, S. G. and Taylor, R. C.].

Secondly, antitumor activity of gallium (III) salts (especially gallium nitrate) has been evaluated in clinidal phase I and phase II trials [Foster et al. Cancer Treat. Rep. 70, 1311–1319, 1986]. Thereafter, gallium nitrate had shown antitumor activity in experimental animal tumors [Adamson et al. Cancer. Chemother. rep. 59, 599–610, 1975]. The phase II trials have shown that gallium nitrate exhibits antitumor activity in patients with refractory lymphomas [FOSTER et al. Cancer Treat. Rep. 70, 1311–1319, 1986].

Another property of gallium nitrate worth mentioning is the fact that it inhibits the reverse transcriptase (an enzyme found in retroviruses) of Rauscher murine leukemia virus in vitro, a virus which belongs to the same viral family as HIV (human immunodeficiency virus). [ Waalkes, T. P. et al. Cancer Res. 34, 385–391, 1974].

However, the preclinical toxicology tests suggest that renal and hepatic damages might be expected with gallium nitrate.

On the other hand, gallium III, administered per os in the form of an aqueous formulation of $GaCl_3$ at the therapeutical dosages involves no renal toxicity [EP-$B_1$-0059 148].

It has now been found that certain gallium (III) complexes have antitumor and antiviral activities.

The invention gallium (III) complexes comprise gallium (III) complexes of N-heterocycles.

More specifically, the gallium (III) complexes of the present invention are selected from the complexes of the following formulae:

1.) Gallium (III)complexes of N-heterocycles

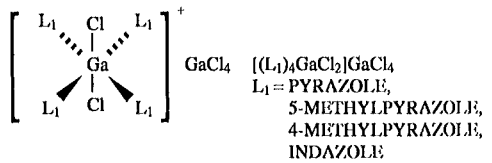

GaCl$_4$   [(L$_1$)$_4$GaCl$_2$]GaCl$_4$
L$_1$ = PYRAZOLE,
5-METHYLPYRAZOLE,
4-METHYLPYRAZOLE,
INDAZOLE
1,2,3,-BENZOTRIAZOLE

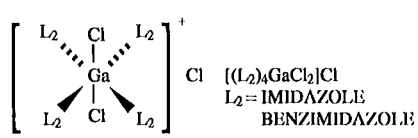

Cl   [(L$_2$)$_4$GaCl$_2$]Cl
L$_2$ = IMIDAZOLE
BENZIMIDAZOLE

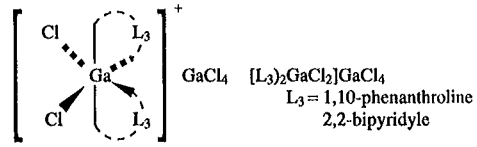

GaCl$_4$   [L$_3$)$_2$GaCl$_2$]GaCl$_4$
L$_3$ = 1,10-phenanthroline
2,2-bipyridyle

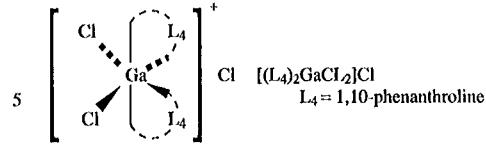

Cl   [(L$_4$)$_2$GaCl$_2$]Cl
L$_4$ = 1,10-phenanthroline

 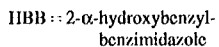

(HBB)GaCl$_2$:    HBB = 2-α-hydroxybenzyl-benzimidazole

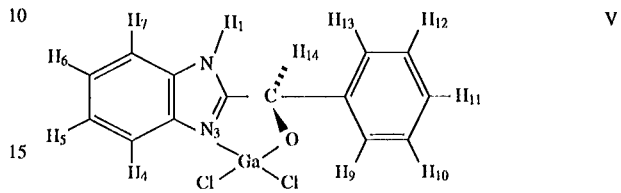

The present invention also relates to the use of the above complexes of formulae I to V as pharmaceutical agents having antiviral and antitumor activities.

The present invention also relates to the use of the following complexes of formula VI as pharmaceutical agents having antiviral and antitumoral activities:

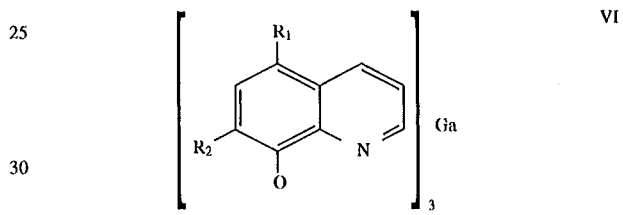

wherein $R_1$ represents hydrogen, a halogen or a sulfono group $SO_3M$, in which M is a metal ion, such as potassium or sodium and $R_2$ represents Hydrogen or $R_1$ is chlorine and $R_2$ is iodo. Said compounds are also gallium III complexes of a N-heterocycle, namely of 8-hydroxy-quinoline.

The compound of formula VI in which $R_1$ is a sulfono group and $R_2$ is hydrogen is new and is a further object of the present invention.

The invention compounds I–V are water-soluble, stable solids, which may exist in the form of enantiomers. The enantiomers are also within the scope of the present invention.

In general, the invention compounds of formulae I to V may be prepared by reacting the ligand L with gallium (III) chloride. The ligand L is firstly dissolved in an inert solvent, optionally under reflux and thereafter a solution of gallium chloride is added; the reaction mixture is advantageously refluxed and cooled gradually to room temperature. If necessary, the so obtained reaction mixture is kept at low temperature, for example 0°–5° C., up to the end of the crystallization. The crystals so formed are then recovered by conventional means.

The compounds of formula VI are prepared by reacting, at room temperature, an appropriate derivative of 8-hydroxyquinoline with a gallium (III) salt, preferably the nitrate or sulfate, and recovering the crystals formed after optional addition of a base, such as potassium hydroxyde or ammonia.

The invention compounds are stable solids, which may exist in the form of enantiomers. The enantiomers are also within the scope of the present invention. The invention compounds are watersoluble, except compounds of formula VT in which $R_1$=H or Cl and $R_2$=H. The compounds of formula VI in which $R_1$=H or Cl and $R_2$=H are soluble in alcohol.

The antitumor and antiviral activities of the invention gallium (III) complexes were determined by the following tests.

ANTITUMOR ACTIVITY

The gallium complexes were administered to animals bearing the P-388 leukaemia or the sarcoma 180 system and the average survival time (T) of the treated animals was compared with the average survival of control animals C. A high value T/C is characteristic of an antitumoral activity.

$$T/C\,(\%) = \frac{\text{average survival of treated animals}}{\text{average survival of control animals}} \times 100$$

ANTIVIRAL ACTIVITY

The gallium (III) complexes were screened for anti-HIV-1 activity at the National Cancer Institute, Bethesda, Md., as part of their in vitro Anti-AIDS Drug Discovery Program. The assay is based on the killing (cytopathic effect) of T4 lymphocytes by human immunodeficiency virus (HIV-1) and is designed to evaluate the drug effects at any stage of the virus reproductive cycle. The system is automated and uses a tetrazolium agent that is metabolically reduced by viable cells to yield a colored formazon product which is measured by colorimetric techniques; a drug with antiviral activity is therefore detected spectrophotometrically when tetrazolium is added after 6 days to produce formazon. All tests are compared with a positive control done at the same time and under identical conditions employing 3'-Azido-3'-deoxythymidine (AZT).

The general procedure is reprinted below from NCI infomation sheets:

1. Candidate agent is dissolved in dimethylsulfoxide, then diluted 1:2000 in cell culture medium. Fuzzchef dilutions (half-$\log_{10}$) are prepared before adding to 96-well microtiter plated.
2. T4 lymphocytes (CEN cell line) are exposed to HIV at a virus-to-cell ratio of approximately 0.05 and are plated along with noninfected control cells into drug-containing wells or wells with medium alone.
3. Cultures are incubated at 37° C. in a 5% carbon dioxide atmosphere for 6 days.
4. The tetrazolium salt, XTT, is added to all wells, and cultures are incubated to allow formazon colour development by viable cells.
5. Individual wells are analysed spectrophotometrically to quantitate formazon production and, in addition, are viewed microscopically for detection of viable cells and confirmation of protective activity.
6. Drug-treated virus-infected cells are compared with drug-treated noninfected cells and with other appropriate controls (untreated infected and untreated noninfected cells, drug-containing wells without cells, etc.) on the same plate.
7. Data reviewed in comparison with other tests done at the same time, and a determination about activity is made.

The invention gallium (III) compounds are preferably formulated into suitable pharmaceutical compositions, such as sterile solutions or suspensions for parenteral administration or as tablets, capsules or elixirs for oral administration (?) with combination of a suitable pharmaceutically acceptable vehicle.

The invention compounds can be administered to patients in need of anti-tumor and anti-vital treatment in a dosage range of 1 to 500 mg per kilogram of body weight per day, preferably administered intraperitoneally, intraveinously and/or orally.

The invention will be now described in more details by the following non-limiting illustrative examples.

The following abbreviations are used in the examples:
pyr=Pyrazole
5-mpyr=5-Methylpyrazole
4-mpyr=4-Methylpyrazole
im=Imidazole
ind=Indazole
benz=1,2,3-Benzotriazole
Bim=Benzimidazole
HBB=2-α-Hydroxybenzylbenzimidazole
M.p=Melting point
MW=molecular weight

EXAMPLES 1 to 5

Synthesis of gallium (III) complexes of N-heterocycles of formula I:$[(L_1)_4\,Ga\,Cl_2]GaCl_4$ 30 to 100 ml of absolute toluene were added to 10 mmol of the ligand and refluxed until the ligand was dissolved. To the clear solution 5 mmol of $GaCl_3$ in the form of the gallium solution were added during a period of 10 minutes; the mixture was refluxed for one hour. The solution was then cooled gradually to room temperature and kept at 5° C. for 2 days. The resulting crystals were filtered off, washed with toluene and ether, and dried under vacuum. Yields were approximately 55%.

EXAMPLE 1 trans-Dichlorotetrakis-(pyrazole)gallium(III) tetrachiorogallate (II)

LIGAND: Pyrazole

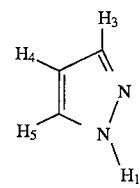

GALLIUM(III) COMPLEX:

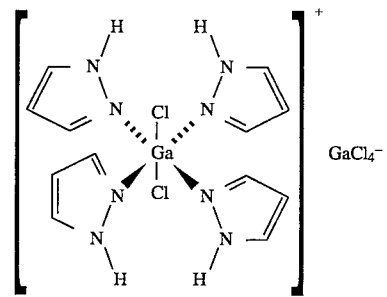

MW = 624.47

The title compound was prepared from 0.5 g (7.34 mmol) of pyrazole and 6.46 ml of a $GaCl_3$ solution (3.67 mmol) in 20 ml absolute toluene by using the general procedure hereinabove described YIELD: 0.6 g (52.4%) of white crystals
Mp: 150°–52° C.
MCROANALYSIS: for [(pyr)$_4$GaCl$_2$]GaCl$_4$:
Calculated: C23.08 H 2.58 N 17.94 Cl 34.06 Ga 22.33
Found: C23.18 H 2.57 N 17.74 Cl 34.10 Ga 22.38
CONDUCTIBILITY: $\lambda_m$=89,5 ohm$^{-1}$ cm$^2$ mol$^{-1}$

EXAMPLE 2 trans-Dichlorotetrakis-(5-methylpyrazole)gallium
(III) tetrachlorogallate (III)

LIGAND: 5-Methylpyrazole

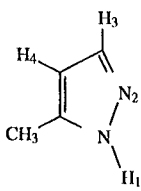

GALLIUM(III) COMPLEX:

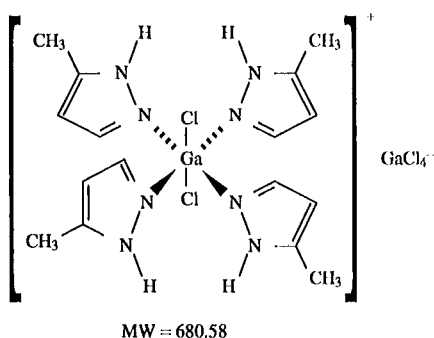

MW = 680.58

The title compound was prepared from 0.5 g 6.09 mmol) of 5-methylpyrazole and 5.4 ml of GaCl$_3$ in solution in 20 ml of absolute toluene.

YIELD: 0.31 g (31%)—white crystals
Mp: 150° C.
MICROANALYSIS: for [(5-mpyr)$_4$GaCl$_2$]GaCl$_4$:
Calculated: C28.24 H 3.55 N 16.46 Cl 31.26 Ga 20.49
Found: C28.22 H 3.62 N 16.42 Cl 29.98 Ga 19.86
CONDUCTIBILITY: $\lambda_m$=93,3 ohm$^{-1}$ Cm$^2$ mol$^{-1}$

EXAMPLE 3 trans-Dichlorotetrakis-(4-methylpyrazole)gallium(II)
tetrachlorogallate(III)

LIGAND: 5-Methylpyrazole

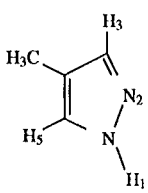

GALLIUM(III) COMPLEX:

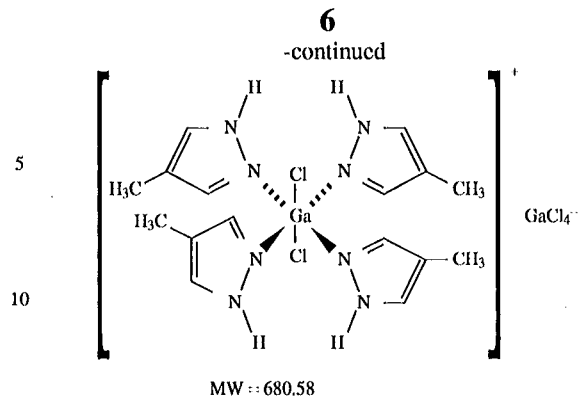

MW = 680.58

The title compound was prepared from 0.5 g (6.09 mmol) of 4-methylpyrzole and 5.4 ml of GaCl$_3$ (3.05 mmol) in 20 ml absolute toluene solution.

YIELD: 0.35 g (33.9%)—white crystals
Mp: 154°–157° C.
MICROANALYSIS: for [(4-mpyr)$_4$GaCl$_2$]GaCl$_4$:
Calculated: C 28.24 H 3.55 N 16.46 Cl 31.26 Ga 20.49
Found: C 28.14 H 3.67 N 16.47 Cl 31.23 Ga 19.56
CONDUCTIBILITY: $\lambda_m$=84,4 ohm$^{-1}$ cm$^2$ mol$^{-1}$

EXAMPLE 4 trans-Dichlorotetrakis-(indazole)gallium(III)
tetrachlorogallate(III)

LIGAND: Indazole

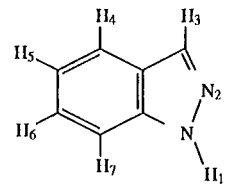

GALLIUM(III) COMPLEX:

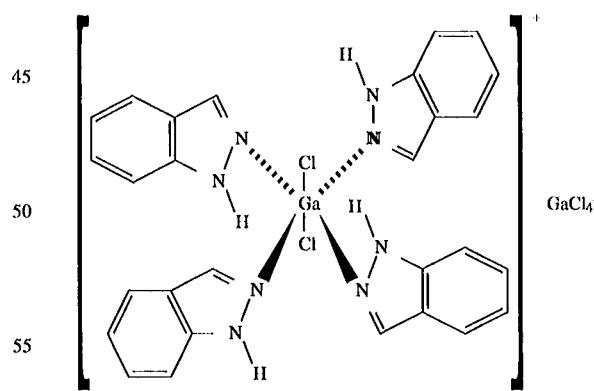

The title compound was prepared from 0.5 g (4.23 mmol) of indazole and 3.72 ml of GaCl$_3$ (2.12 mmol)

YIELD: 0.35 g (51.6%) brown crystals
Mp: 166°–168° C.
MICROANALYSIS: for [(ind)$_4$GaCl$_2$]GaCl$_4$:
C 28.24 H 3.55 N 16.46 Cl 31.26 Ga 20.49
C 28.14 H 3.67 N 16.47 Cl 31.23 Ga 19.56
CONDUCTIBILITY: $\lambda_m$=84,6 ohm$^{-1}$ cm$^2$ mol$^{-1}$

EXAMPLE 5 trans-Dichlorotetrakis-(1,2,3-benzotriazole)gallium(III) tetrachlorogallate(III)

LIGAND: 1,2,3-Benzotriazole

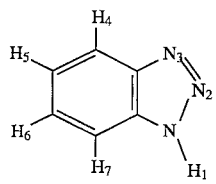

GALLIUM(III) COMPLEX:

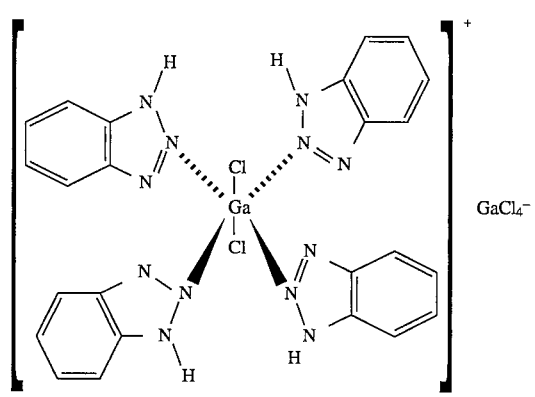

MW = 828.67

STARTING PRODUCTS:

0.5 g (4.20 mmol) 1,2,3-benzotriazole 3.5 ml $GaCl_3$ solution (2.10 mmol)

20 ml absolute Toluene

YIELD: 0.41 g (47%)—white crystals

M.p.: 139° C.

MICROANALYSIS for $[(benz)_4GaCl_2]GaCl_4$:

Calculated: C 34.79 H 2.43 N 20.28 Cl 2567 Ga 16.83

Found: C 35.06 H 2.54 N 20.58 Cl 25.19 Ga 16.06

CONDUCTIBILITY: $\lambda_m = 83.0$ ohm$^{-1}$ cm$^2$ mol$^{-1}$

The IR- and $^1$H NMR-data of the complexes of Examples 1 to 5 are gathered in the following Tables I and II.

TABLE I

| | IR-data for $[(L_1)_4Ga\ Cl_2]\ Ga\ Cl_4$ in cm$^{-1}$ | | | | |
|---|---|---|---|---|---|
| Complex | ν(N—H) | ν(=C—H) | ν(Ga—Cl) for $GACl_1^-$ | ν(Ga—Cl) for $[L_1GaCl_2]^+$ | ν(Ga—N) |
| General formula/$(L_1)_4GACL_2/GACL_4$ | | | | | |
| $[(pyr)_4GaCl_2]GaCl_4$ | 3346(s) | 3143(s) | 375(s) | 295(s) | 246(m),209(w) |
| $[(5\text{-mpyr})_4GaCl_2]GaCl_4$ | 3340(s) | 3140(m) | 382(s) | 300(m) | 285(m),229(s) |
| $[(4\text{-mpyr})_2GaCl_2]GaCl_4$ | 3375(s),3320(s) | 3122(s) | 374(s) | 319(s) | 277(m),218(m) |
| $[(ind)_4GaCl_2]GaCl_4$ | 3331(s) | 3126(m),3073(w) | 379(s) | 297(s) | 250(m),204(m) |
| $[(benz)_4GaCl_2]GaCl_4$ | 3230(s) | 3050(w) | 381(s) | 354(s) | 323(m),250(w) |

(s) = strong
(m) = middle
(w) = weak

TABLE II

| Compounds | $H_3$ | $H_4$ | $H_5$ | $H_6$ | $H_7$ | solvent |
|---|---|---|---|---|---|---|
| $^1$H-NMR data for $[(L_1)_4GaCl_2]GaCl_4$ and ligands L (in ppm-reference TMS) | | | | | | |
| General formula $[(L_1)_4GACL_2]GACL_4$ | | | | | | |
| $[(pyr)_4GaCl_2]GaCl_4$ | 7.90(d) | 6.55(d) | 7.90(d) | · · | · · | $D_2O$ |
| pyr | 7.20(d) | 5.90(d) | 7.20(d) | · · | · · | $D_2O$ |
| $[(3\text{-mpyr})_4GaCl_2]GaCl_4$ | · · | 6.30(d) | 7.75(d) | · · | · · | $D_2O$ |
| 5-mpyr | · · | 5.45(d) | 6.95(d) | · · | · · | $D_2O$ |
| $[(4\text{-mpyr})_4GaCl_2]GaCl_4$ | 7.7(s) | · · | 7.7(s) | · · | · · | $D_2O$ |
| 4-mpyr | 7.0(s) | · · | 7.0(s) | · · | · · | $D_2O$ |
| $[(ind)_4GaCl_2]GaCl_4$ | 8.3(s) | 7.7(d) | 7.55(t) | 7.30(t) | 7.95(d) | $D_2O$ |
| ind | 8.23(s) | 7.7(d) | 7.55(t) | 7.30(t) | 7.95(d) | $D_2O$ |
| $[(benz)_4GaCl_2]GaCl_4$ | · · | 7.90(d) | 7.50(d) | 7.50(d) | 7.90(d) | $CD_3OD$ |
| benz | · · | 7.90(d) | 7.50(d) | 7.50(d) | 7.90(d) | $CD_3OD$ |

(s) = singlet, (d) = doublet, (t) = triplet

EXAMPLES 6 to 7

Synthesis of gallium(III) complexes of
N-heterocycles of formula II: $[(L_2)_4Ga\,Cl_2]$ Cl 50 to 100 ml of absolute toluene were added to 10 mmol of the ligand and refluxed until the ligand was dissolved. To the clear solution 2.5 mmol of $GaCl_3$ in the form of the gallium solution were added during a period of 10 minutes; the mixture was refluxed for one hour. The solution was then cooled gradually to room temperature and kept at 5° C. for 2 days. The resulting precipitate was filtered off, washed with toluene and ether, and dried under vacuum. Yields were approximately 50%.

EXAMPLE 6 trans-Dichlorotetrakis-(imidazole)gallium(II) chloride

LIGAND: Imidazole

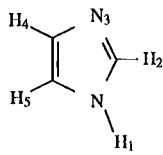

GALLIUM(III) COMPLEX:

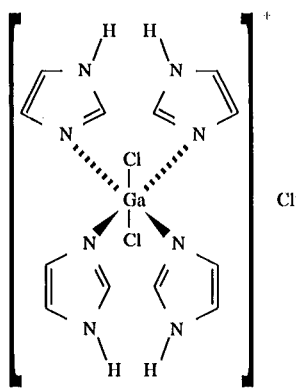

MW = 448.39

STARTING PRODUCTS:

0.5 g (7.35 mmol)imidazole 3.24 ml $GaCl_3$-solution (1.84 mmol)

20 ml absolute toluene

YIELD: 0.35 g (42.5%)—white and hygroscopic powder

M.p.: 190°–195° C.

MICROANALYSIS: for $[(im)_4GaCl_2]Cl$:

Calculated: C 32.14 H 3.59 N 24.99 Cl 23.72 Ga 15.55

Found: C 32.75 H 3.66 N 24.69 Cl 22.35 Ga 15.32

CONDUCTIBILITY: $\lambda_m$=54.5 ohm$^{-1}$ cm$^2$ mol$^{-1}$

EXAMPLE 7 trans-Dichlorotetrakis-(benzimidazole)gallium(III) chloride

LIGAND: Benzimidazole

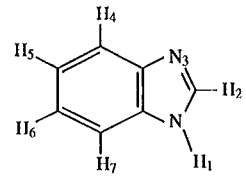

GALLIUM(III) COMPLEX:

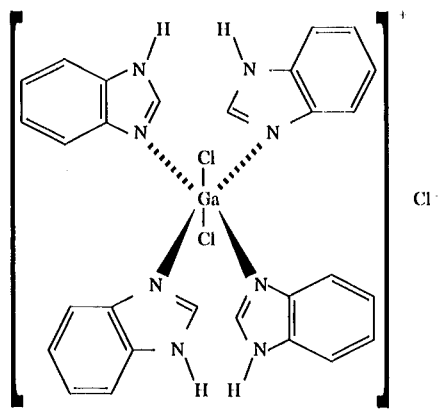

MW = 648.63

STARTING PRODUCTS:

0.5 g (4.23 mmol)benzimidazole 1.86 ml $GaCl_3$-solution (1.06 mmol)

30 ml absolute toluene YIELD: 0.39 g (56.9%)—white and hygroscopic powder

MICROANALYSIS: for $[(bim)_4GaCl_2]Cl$:

Calculated: C 51.85 H 3.73 N 17.28 Cl 16.40 Ga 10.75

Found: C 51.61 H 4.35 N 17.07 Cl 14.60 Ga 8.77

CONDUCTIBILITY: $\lambda_m$=49.6 $ohm^{-1}$ $cm^2$ $mol^{-1}$

The IR- and $^1$H-NMR data of complexes of Examples 6 and 7 are given in the following tables III and IV.

TABLE III

| | IR data for $[(L_2)_4GaCl_2]$ in $v = cm^{-1}$ | | |
|---|---|---|---|
| | v(N—H) | v(Ga—Cl) $[L_4GaCl_2]^+$ | v(Ga—N) |
| General formula: $[(L_2)_4GACL_2]Cl$ | | | |
| $[(im)_4GaCl_2]Cl$ | 3180(s) | 278(m) | 226(w)? |
| $[(bim)_4GaCl_2]Cl$ | 3401(m) | 310(m) | 276(m)? |

(s) = strong, (m) = middle, w = weak ? = allocation doubtful

TABLE IV

| $^1$H - NMR data for $[(L_2)_4GaCl_2]Cl$ and the ligand L (in ppm - width TMS as reference) | | | | | | |
|---|---|---|---|---|---|---|
| Compound | $H_2$ | $H_4$ | $H_5$ | $H_6$ | $H_7$ | Solvent |
| General formula $[(L_2)_4GACL_2/CL$ | | | | | | |
| $[(im)_4GaCl_2]Cl$ | 8.55(s) | 7.45(s) | 7.45(s) | — | — | $D_2O$ |
| im | 7.65(s) | 7.05(s) | 7.05(s) | — | — | $D_2O$ |
| $[(bim)_4GaCl_2]Cl$ | 9.0(s) | 7.75(m) | 7.95(m) | 7.90(m) | 7.75(m) | $D_2O$ |
| bim | 8.45(s) | 7.55(m) | 7.90(m) | 7.90(m) | 7.55(m) | $D_2O$ |

(s) = singlet, (d) = doublet, (t) = triplet, (m) = multiplet

EXAMPLE 8

Dichloro-(2-α-oxybenzimidazolato-N,O)gallium(III)

LIGAND: 2- -Hydroxybenzyl-benzimidazole: HBB.

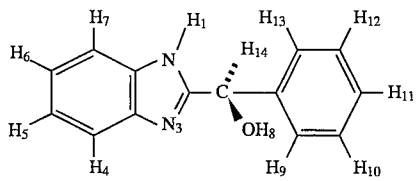

GALLIUM(III) COMPLEX

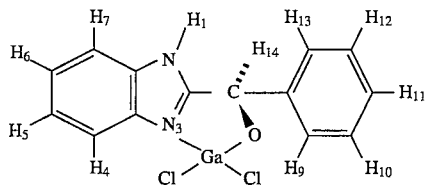

General procedure for the synthesis of gallium(III) complexes of the general formula $LGaCl_2$/L=2-α-hydroxybenzylbenzimidazole (HBB), D(−)-2α-hydroxybenzylbenzimidazole (D(−)-HBB), L(+)-2-α-hydroxybenzylbenzimidazole (L(+)-HBB)/.

2 mmol of the ligand were dissolved in 450 ml of absolute ether under reflux. To the clear solution 2 mmol of $GaCl_3$ in the form of the gallium solution were added during a period of 2 minutes; the first drops of the gallium solution produced a turbidity which disappeared when more of the gallium solution was added. After all of the gallium solution had been added, the solution was cooled to room temperature and kept at 0° C. for 2 days. The resulting crystals were filtered off, washed with ether, and dried under vacuum. Yields were approximately 45%.

Synthesis of HBB and of the enantiomers (D(−)-HBB and L(+)-HBB.

2-α-hydroxybenzylbenzimidazole (HBB) could be synthesized according to (Philips, M. A. J. Chem. Soc. 2393, 1928). The preparation of the enantiomers (−)-HBB and (+)-HBB proved to be difficult, however. Especially, the isolation of the enantiomers following the literature procedure (8b) was tedious and led to unsatisfactory results producing the racemate.

Therefore, the following procedure was employed for synthesis of the enantiomers:

4.56 g (0.03 mol) of D(−)- or L(+)-mandelic acid (both purchased from Fluka) and 2.16 g (0.02 mol) of 1,2-phenylendiamine were dissolved in 20 ml of 4N hydrochloric acid and refluxed for 8 hours under an argon stream. The solution was then allowed to cool to room temperature and was put into the refrigerator (5° C.) for one hour. A white precipitate was formed, which can be increased by adding a few drops of 4N HCl. The precipitate was filtered off and then dissolved in 30 ml of water. This clear solution was neutralized with 20% $K_2CO_3$ and a white precipitate was formed, which was filtered off and washed with water. This precipitate was recrystallized twice from ethanol/water=1:1 to produce the respective enantiomers as white crystals:

D(−)-HBB: $C_{14}H_{12}N_2O$ found (%) C 74.45 H 5.45 N 12.34 calculated (%): C 74.98 H 5.40 N 12.50

L(+)-HBB: $C_{14}H_{12}N_2O$ found (%): C 74.93 H 5.43 N 12.34 calculated (%): C 74.98 H 5.40 N 12.45

The optical rotation value $[\alpha]_D$ for the enantiomers measured in absolute ethanol were very low.

D(−)-HBB: $[\alpha]_D$=−2.41°–T=20° C.

L(+)-HBB: $[\alpha]_D$=+2.05°–T=20° C.

Measured in absolute acetone, however, they were considerably higher:

D(−)-HBB: $[\alpha]_D$=−30.2°=20° C.

L(+)-HBB: $[\alpha]_D$=+29.1°–T=20° C.

To make sure that the compounds were in fact the enantiomers, we synthesized the hydrochlorides (for which the literature values for [α]_D are known (8b)) from the obtained products by dissolving 100 mg in 200 ml of absolute ether and saturating the solution with a stream of dry HCl. A white substance precipitated, which was filtered off and recrystallized once from isopropyl alcohol/ether= 1:1, and the following optical rotation values were obtained at T=20° C.

D(−)-HBB*HCl: $[\alpha]_D=-83.6°$ (water) Lit.: $[\alpha]_D=-82.7°$ (water)

L(+)-HBB*HCl: $[\alpha]_D=+84.5°$ (water) Lit.: $[\alpha]_D=+83.2°$ (water)

This observation proves that the free ligands D(−)-HBB and L(+)-HBB, which were isolated are indeed the pure enantiomers despite their low optical rotation in ethanol.

A—Dichloro-(2-α-oxybenzylbenzimidzoiato-N,O)gallium(III)

STARTING PRODUCTS:

250 mg (1.12 mmol)HBB 1.96 ml (1.12 mmol) of ether solution of GaCl_3 diluted with 10 ml absolute ether.

230 ml absolute ether

YIELD: 150 mg (60%)

M.p.: 223°–226° C.

MICROANALYSIS for (HBB)GaCl_2:
Calculated: C 46.21 H 3.05 N 7.70 Cl 19.49 Ga 19.16
Found: C 46.34 H 3.54 N 7.61 Cl 18.80 Ga 18.67
CONDUCTIBILITY: $\lambda_m=23.75$ ohm$^{-1}$ cm$^2$ mol$^{-1}$ B—Dichloro-(D(−)-2-α-oxybenzylbenzimidazolato-N, O)gallium(III)

YIELD: 141 g (56%)
M.p.: 227°–230° C.

MICROANALYSIS for (D(−)-HBB)GaCl_2:
Calculated: C 46.21 H 3.05 N 7.70 Cl 19.49 Ga 19.16
Found: C 45.78 H 3.38 N 7.31 Cl 18.38 Ga 18.59
CONDUCTIBILITY: $\lambda_m=28.75$ ohm$^{-1}$ cm$^2$ mol$^{-1}$ C—Dichloro-(L(+)-2-α-oxybenzylbenzimidazolato-N, O)gallium(III)

YIELD: 172 g (69%)
M.p.: 224°–228° C.

MICROANALYSIS for (L(+)-HBB) GaCl_2:
Calculated: C 46.21 H 3.05 N 7.70 Cl 19.49 Ga 19.16
Found: C 46.00 H 3.27 N 7.79 Cl 19.29 Ga 18.24
CONDUCTIBILITY: $\lambda_m=25.0$ ohm$^{-1}$ cm$^2$ mol$^{-1}$ Optical rotation of (D(−)-HBB)GaCl_2 and (L-(+)-HBB)GaCl_2. The optical rotation values of the gallium (III) complexes of the enantiomers D(−)-HBB and L(+)-HBB were determined in distilled water:

(D(−)-HBB)GaCl_2: $[\alpha]_D=-6.2°$—T=20° C.
(L(+)-HBB)GaCl_2: $[\alpha]_D=+5.9°$—T=20° C.

These values are not very high but they increased considerably when the optical measurements were carried out in ethanol showing that the optical rotation values of these complexes are highly solvent-dependent:

$[\alpha]_D$ in ethanol:
(D(−)-HBB)GaCl_2: $[\alpha]_D=+126.0°$—T=20° C.
(L(+)-HBB)GaCl_2: $[\alpha]_D=+126.0°$—T=20° C.

The IR- and NMR-data of the above (HBB) GaCl_2 complexes are given in the following tables V and VI.

TABLE 5

| Complex | v(N—H) | v(=C—H) | v(Ga—O) | v(Ga—Cl) |
|---|---|---|---|---|
| (HBB)GaCl_2 | 3336(m) | 3058(m), 3029(m) | 650(m) | 376(s), 290(s) |
| (D(−)-HBB)GaCl_2 and (L(+)-HBB)GaCl_2-see (HBB)GaCl_2 | | | | |

IR data for (HBB) GaCl_2 (in v = cm$^{-1}$)

(s) = strong, (m) = middle, (w) = week

TABLE VI

| Compound | H_4, H_5, H_6, H_7, H_10, H_11, H_12 | H_9, H_13 | H_14 | Solvent |
|---|---|---|---|---|
| (HBB)GaCl_2 | 7.30–7.60(m) | 7.75(m) | 6.25(s) | CD_3OD |

| Compound | H_4, H_5, H_6, H_7 | H_9, H_10, H_11, H_12, H_13 | H_14 | Solvent |
|---|---|---|---|---|
| HBB | 7.5(d) | 7.10–7.30(m) | 6.0(s) | CD_3OD |
| (D(−)-HBB)GaCl_2 and (L(+)-HBB)GaCl_2 - see (HBB)GaCl_2 | | | | |

(s) = singlet, (d) = doublet, (t) = triplet, (m) = multiplet

EXAMPLES 9 to 11

Synthesis of Gallium(III) complexes of 8-Hydroxyquinolines

EXAMPLE 9

Tris-(8-Hydroxyquinoline)gallium

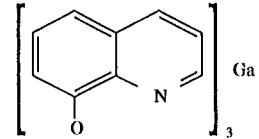

Synthesis: 14.0 g (96.4 mmol) of 8-hydroxyquinoline (dissolved in 500 g of 10% acetic acid) were added to 7.54 of gallium(III)nitrate/Ga(NO 3)3*H2O/(27.6 mmol) at room temperature. The solution was then stirred and heated to T=80° C. under reflux. Concentrated ammonia was added until the pH-value was 7, and a yellow precipitate was formed. The suspension was then refluxed for one hour. The yellow precipitate was filtered off, washed with hot and cold water and dried at T=100° C. in a drying oven. The yield was 90%.

EXAMPLE 10

Tris-(5-chloro-7-iodo-B-hydroxyquinoline)gallium-(III):(known from literature)

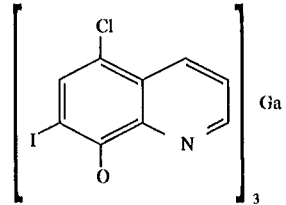

Synthesis: 0.46 g (1.1 mmol) of gallium(III)sulfate were dissolved in 200 ml of distilled water by stirring, the pH-value adjusted to 1 with concentrated sulfuric acid, and the solution heated to T= 90° C. To this solution 2.0 g (6.5 mmol) of 5-Chloro-7-iodo-8-hydroxyquinoline (dissolved in 100 m of acetone) were added; a yellow precipitate formed immediately. The suspension was allowed to cool to T=50° C.; then the yellow precipitate was filtered off, washed with hot water/acetone=1:1 and dried at T=120° C. in a drying oven. The yield was 91%.

EXAMPLE 11

Synthesis of Tris-(5-sulfono-8-hydroxyquinoline)-gallium(III)-potassium salt

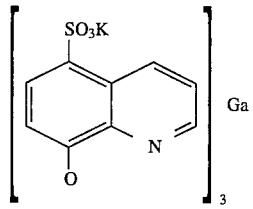

925.4 mg (3.8 mmol) of 8-Hydroxyquinoline-5-sulfonic acid and 300 mg of Gallium(III)nitrate/Ga(NO$_3$)$_3$, n H$_2$O/ (1.2 mmol) were suspended at room temperature. To this suspension 374 mg (6,7 mmol) of potassium hydroxide-(KOH) were added resulting in a clear solution. Half of the solvent was evaporated and the clear solution put into a refrigerator at T=5° C. After 2 days white crystals were formed, which were filtered off, washed with a little ethanol and dried under vacuum. The yield was 40%.

PHARMACOLOGICAL RESULTS

1—Antitumor Activity

Gallium(III) complexes of 1,10 phenanthroline of formulae III and IV, known from literature, [C. Norman et al., J. Am. Chem. Soc, 77, 5225 (1955)], showed a T/C value of 126–128% in the P 388 system. Similarly, (HBB)GaCl$_2$ complex possesses a T/C value of 130%.

On the other hand, gallium(III) complexes of 8-hydroxyquinoline showed high plasma uptake and an antitumor activity of T/C=138% in the sarcoma 180 system.

Gallium (III) complex of 5-sulfono-8-hydroxyquinoline showed an antitumor activity of T/C=153% in the sarcoma 180 system.

2—Antiviral Activity

The anti-viral activity was determined by the protocol hereinabove disclosed for certain complexes of the invention. The results are given in the following Table VII.

TABLE VII

| Complex | EC$_{50}$ (in mol) | IC$_{50}$ | TI = IC$_{50}$/EC$_{50}$ (in mol) | Cellular line |
|---|---|---|---|---|
| [(3-mpyr)$_4$GaCl$_2$]GaCl$_4$ | 1.08 × 10$^{-4}$ | 1.64 × 10$^{-4}$ | 1.52 | CEM-6 |
| [(4-mpyr)$_4$GaCl$_2$]GaCl$_4$ | 2.31 × 10$^{-4}$ | 2.56 × 10$^{-4}$ | 1.11 | CEM-6 |
|  | 5.02 × 10$^{-5}$ | 1.97 × 10$^{-4}$ | 3.92 | CEM-IW |
| (HBB)GaCl$_2$ | 4.30 × 10$^{-5}$ | 2.21 × 10$^{-4}$ | 5.14 | CEM-IW |
| [(bim)$_4$GaCl$_2$]Cl | 5.01 × 10$^{-6}$ | 3.85 × 10$^{-4}$ | 76.9 | CEM-6 |
| AZT | 1.86 × 10$^{-7}$ | 1.91 × 10$^{-4}$ | 1027 | CEM-SS(*) |
| (3'-azido-2,3'-deoxythymidine | 1.87 × 10$^{-7}$ | 6.89 × 10$^{-4}$ | 3680 | CEM(**) |

(*) = Values from O. S. Weislow et al. [L. MUSLIN et al. Halv. Chim. Acta 36 (111), 886–890 (1953)
(**) = Values from R. Vince et al. [R. VINCE et al., Biochem. Biophys. Res. Commun. 156, 1046-1053, (1988)

We claim:

1. Method for treatment of viral infections or tumors sensitive to gallium treatment, comprising administering a gallium complex of the formula:

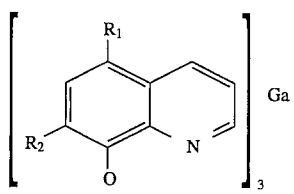

wherein R$_1$ represents hydrogen, a halogen or a sulfono group SO$_3$M, in which M is a metal ion, and R$_2$ represents hydrogen, or R$_1$ is chlorine and R$_2$ is iodo.

2. Method according to claim 1, wherein the metal ion is potassium or sodium.

3. Pharmaceutical composition containing as active principle an effective amount of a compound of the formula:

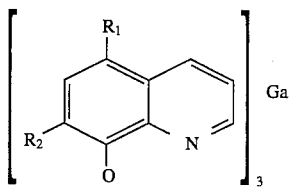

wherein R$_1$ represents hydrogen, a halogen or a sulfono group SO$_3$M, in which M is a metal ion, and R$_2$ represents hydrogen, or R$_1$ is chlorine and R$_2$ is iodo, in combination with a pharmaceutically acceptable vehicle.

4. Pharmaceutical composition according to claim 3, wherein the metal ion is potassium or sodium.

* * * * *